(12) United States Patent
Goodman et al.

(10) Patent No.: US 7,028,893 B2
(45) Date of Patent: Apr. 18, 2006

(54) FINGERPRINT BASED SMARTCARD

(75) Inventors: Cathryn E. Goodman, Glen Ellyn, IL (US); Mark Lill, Elgin, IL (US); Behnam Bavarian, Newport Coast, CA (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 11/009,509

(22) Filed: Dec. 10, 2004

(65) Prior Publication Data

US 2005/0150947 A1    Jul. 14, 2005

Related U.S. Application Data

(60) Provisional application No. 60/530,698, filed on Dec. 17, 2003.

(51) Int. Cl.
*G06K 5/00*    (2006.01)

(52) U.S. Cl. ..................... 235/380; 235/382

(58) Field of Classification Search ............... 235/380, 235/381, 382, 385, 441, 451, 487, 492
See application file for complete search history.

(56) References Cited

U.S. PATENT DOCUMENTS

| | | |
|---|---|---|
| 4,353,056 A | 10/1982 | Tsikos |
| 4,814,690 A | 3/1989 | Melcher et al. |
| 5,509,083 A | 4/1996 | Abtahi et al. |
| 5,599,391 A | 2/1997 | Lee |
| 5,603,179 A | 2/1997 | Adams |
| 5,613,012 A | 3/1997 | Hoffman et al. |
| 5,613,712 A | 3/1997 | Jeffers |
| 5,615,277 A | 3/1997 | Hoffman |
| 5,623,552 A * | 4/1997 | Lane ........................ 382/124 |
| 5,625,448 A | 4/1997 | Ranalli et al. |
| 5,629,889 A | 5/1997 | Chandra et al. |
| 5,659,613 A | 8/1997 | Copeland et al. |
| 5,665,193 A | 9/1997 | Groswith, III et al. |
| 5,668,603 A | 9/1997 | Copeland |
| 5,668,874 A | 9/1997 | Kristol et al. |
| 5,729,334 A | 3/1998 | Van Ruyven |
| 5,738,449 A | 4/1998 | Groswith, III et al. |
| 5,739,864 A | 4/1998 | Copeland |
| 5,799,092 A | 8/1998 | Kristol et al. |

(Continued)

FOREIGN PATENT DOCUMENTS

EP     1 018 695 A2    12/1999

(Continued)

OTHER PUBLICATIONS

"FingerChip™ The world's smallest therman silicon chip fingerprint sensor", Atmel Corporation, www.atmel.com (pages).

(Continued)

*Primary Examiner*—Daniel Stcyr
(74) *Attorney, Agent, or Firm*—Valerie M. Davis (57) ABSTRACT

A smartcard device 1200 that includes a single embedded IC chip 1222 that includes smart card circuitry that includes a processor device and memory that is shared with a fingerprint capture device (10) that has a plurality of charge storage devices (12), i.e., the shared memory, that couple through conductive surfaces (22) to conductive spheres (21) that are disposed within an epoxy that comprises a fingerprint contact surface (13). When raised portions of an object (26) appropriately contact certain conductive spheres (21), the corresponding charge storage device (12) will discharge through a separate conductive sphere which is connected to a grounded conductive surface. This discharging serves both to simultaneously sense the asperity features of the object and to store that sensed information as well.

19 Claims, 6 Drawing Sheets

U.S. PATENT DOCUMENTS

| | | | |
|---|---|---|---|
| 6,049,763 | A | 4/2000 | Christiansen et al. |
| 6,088,471 | A | 7/2000 | Setlak et al. |
| 6,320,394 | B1 | 11/2001 | Tartagni |
| 6,325,285 | B1 * | 12/2001 | Baratelli ................ 235/380 |
| 6,376,393 | B1 | 4/2002 | Newton et al. |
| 6,442,286 | B1 * | 8/2002 | Kramer ................ 382/124 |
| 6,513,709 | B1 * | 2/2003 | Hansen ................ 235/380 |
| 6,651,149 | B1 * | 11/2003 | Iwasaki ................ 711/163 |
| 6,776,332 | B1 * | 8/2004 | Allen et al. ............. 235/380 |
| 2003/0108226 | A1 | 6/2003 | Goodman et al. |
| 2003/0203543 | A1 | 10/2003 | Tanabe et al. |
| 2004/0125990 | A1 | 7/2004 | Goodman et al. |

FOREIGN PATENT DOCUMENTS

| | | |
|---|---|---|
| WO | WO 00/68874 | 11/2000 |

OTHER PUBLICATIONS

James L. Wayman, "Fundamentals of Biometric Technologies", U.S. National Biometric Test Center (33 pages).

"BioMouse™—Desktop Fingerprint Scanner" © 1996-2000 DEW Engineering and Develpoment Limited, American Biometric Company (3 pages).

"FPS110 Silicon Fingerprint Sensor" © 1997-2000, Veridicom, Inc. (4 pages).

"AF-S2 FingerLoc Fingerprint Sensor", © 1998-2001 Authen Tec, Inc. (4 pages).

"BioLogon 1.0 Fingerprint Identification Technology" © 1998 Identicator Technology www.identicator.com (20 pages).

"Fujitsu Introduces Finger Pass Card, a PC Card-Based Fingerprint Recognition Device for Mobile PC's", 1998, Fijitsu Limited (2 pages).

"A Technology to Make Passwords a Thing of the Past", *The Wall Street Journal,* Nov. 12, 1998 (1 page).

Kim Komando, "Protect Your PC With Just a Fingertip", © 1998 *Los Angeles Times syndicate* (1 page).

Margaret Quan, "Fingerprint Sensor Looks to Tap Security Applications", *EE Times,* Oct. 4, 1998 (2 pages).

"Motorola, Identix Announce New Biometric Fingerprint Reader Which Sets New Industry Standards for Size, Security and Cost", Nov. 30, 1999, apspg.motorola.com/press/links (2 pages).

Mike Maharry, "Positive ID—Firm uses biometrics, hand scans in new identification system", *the Tacoma News Tribune,* Aug. 7, 2000 (2 pages).

"The Technology in Brief", Authen Tec, Inc. Personal Security for the Real World™ © Authen Tec, Inc. (4 pages).

Booth 1906 Exhibit Description: "Enix's fingerprint sensor employs the fimr's . . . ", Enix Corp., F Project, Marketing Div., 2000 91 page).

"Thermal Fingerprint Sensor with 0.4 mm×14 mm (0.02"×0.55") Sensing Area and Digital Output (on-chip ADC)"—FDC4A14 FingerChip ™, Amtel, Rev. 1962A-01-2000.

"How it Works", www.veridicom.com, Veridicom—World Leader in Fingerprint Authentication Technology, Nov. 13, 2001 (2 pages).

"AFS8500 FingerLoc™ FingerPrint Sensor", © 2002 Authen Tec, Inc. (2 pages).

MBF300 Solid State Fingerprint Sweep Sensor™, 2002 Fujitsu Microelectronics America, Inc. (37 pages).

"Fingerprint Imaging Sensor Product Data Sheet FIS-3001", Nov. 2002, Fidelica Microsystems, Inc. (6 pages).

"TouchPrint™ 3000 Live Scan" Data Sheet, Rev. A 05/03, Identix Public Sector (2 pages).

P.L. Rolandi, et al., "IM-Cell 6b/Cell Analog Flash Memory for Digital Storage, " ISSCC 1998, Columns 1 and 2, Figures 1-2 (3 pages).

A. Kramer, et al., "1.5TXPS Convolver Using 5b Analog Flash for Real-Time Large-Kernel Image Filtering," ISSCC 1998, Columns 1 and 2, Figure 2 (2 pages).

* cited by examiner

FINGERPRINT BASED SMARTCARD

FIELD OF THE INVENTION

This invention relates generally to smartcards having embedded fingerprint authentication capabilities.

BACKGROUND OF THE INVENTION

Fingerprints are well understood to be unique to an individual and are therefore useful for identification and verification purposes. The surface asperities (that is, the ridges and valleys) that constitute a fingerprint can be sensed and imaged in a variety of ways and used thereafter to compare with previously stored fingerprint information for these purposes.

A fingerprint offers a reliable and inexpensive means of authenticating an individual's identity. Thus, fingerprint identification systems have played a critical role in modern society in both civil and criminal applications. For example, criminal identification in public safety sectors is an integral part of any present day investigation. Similarly in civil applications such as credit card or personal identity fraud, fingerprint identification has become an essential part of the security process.

One known application for fingerprint identification and authentication is in association with a smartcard. In such an application, a fingerprint authentication module is embedded in a smartcard. The fingerprint authentication module is typically a set of self-contained integrated circuit ("IC") chips that comprise all elements necessary for: performing an enrollment algorithm for a user for capturing, enrolling and storing an initial fingerprint image against which other fingerprints will be verified; capturing a subsequent fingerprint image for use in the verification stage; and performing an algorithm for comparison with the stored fingerprint image and user authentication. Thus, the fingerprint module typically includes a sensor device, a processing device and a memory device. Once the fingerprint of the authorized user has been verified, a separate smartcard IC chip, also embedded in the smartcard, may be automatically activated to proceed and establish communications with a host system.

The above-described smartcards with embedded fingerprint authentication systems have a number of limitations. For instance, the fingerprint authentication module is a completely separate set of IC chips from the smartcard chip. This increases the cost of the smartcard since separate pieces of silicon must be used for each IC chip. This also increases the power consumption of the smartcard due to the separated IC chips.

Another limitation of these smartcards having fingerprint authentication is that the two IC chips are typically located on opposite ends of the smartcard. Accordingly in an application where the smartcard IC establishes communications with the host device via a contact-less means such as, for instance, radio frequency communication, the circuitry needed to connect the two chips typically limits the area available for an antenna at the desirable frequency and with sufficient gain so that the smartcard may be positioned an adequate distance from a reader device and still retain operability.

Another limitation of two separate chips, one for smart card functions and one for sensor functions, is that there is a physical interconnection path between the two which is subject to security violations. For example, inserting another person's fingerprint into the system.

Yet another limitation is that the sensor on the fingerprint authentication chip is typically capacitance based. Capacitance based mechanisms offer relatively good asperity detection but are susceptible to electrostatic discharge that can impair or destroy the mechanism. Many such mechanisms must utilize titanium nitride materials to protect against such electrostatic discharge and this complicates manufacturability. Furthermore, such capacitance based mechanisms typically require a considerable amount of processing capability to convert the sensed asperities into storable data. In addition to the limitations of capacitance based sensors in capturing a fingerprint, there are limitations in the ability to integrate capacitive based sensors with a smart card. For example, capacitive sensors require operational amplifiers for processing that are not normally contained within a smart card IC. Addition of these devices would substantially increase the cost, size, and power consumption of the smart card IC.

A need therefore exists for a cost-effective smartcard having fingerprint authentication capabilities, which does not require separate smartcard and fingerprint authentication IC chips. It is further desired that the smartcard have suitable and cost-effective means for protecting itself against electrostatic discharge.

BRIEF DESCRIPTION OF THE FIGURES

A preferred embodiment of the invention is now described, by way of example only, with reference to the accompanying figures in which.

DETAILED DESCRIPTION OF THE INVENTION

While this invention is susceptible of embodiments in many different forms, there are shown in the figures and will herein be described in detail specific embodiments, with the understanding that the present disclosure is to be considered as an example of the principles of the invention and not intended to limit the invention to the specific embodiments shown and described. Further, the terms and words used herein are not to be considered limiting, but rather merely descriptive. It will also be appreciated that for simplicity and clarity of illustration, elements shown in the figures have not necessarily been drawn to scale. For example, the dimensions of some of the elements are exaggerated relative to each other. Further, where considered appropriate, reference numerals have been repeated among the figures to indicate corresponding elements.

Viewed generally, the embodiments described below comprise a fingerprint based smartcard IC. As used herein, "fingerprints" is used generically to refer to any surface having asperities or other similar surface variations capable of producing a patterned tactile impression, including but not limited to fingerprints, palm prints, and glove prints.

In one embodiment, the invention comprises a smartcard having embedded therein a single IC chip for both fingerprint authentication and smartcard capabilities such as, for instance, establishing communication with a host system. The single IC chip includes a fingerprint capture device integrated with smartcard circuitry that includes at least one memory device and a conventional smartcard processing device. Thus, the fingerprint capture device has a shared a memory with the smartcard circuitry and also includes a fingerprint contact surface. Any processing functionality associated with the fingerprint capture device, such as, for instance, an enrollment algorithm for capturing the initial fingerprint of the user and verification and matching algorithms for comparing a subsequently captured print, is shared with the smartcard's processor functionality.

The memory is comprised of a plurality of memory cells wherein each memory cell has a corresponding electrical device. The fingerprint contact surface is disposed substantially coplanar to the memory and has a plurality of conductive paths formed therethrough. At least some of these conductive paths are conductively coupled to at least some of the corresponding electrical devices in the memory cells. In one embodiment, the electrical devices are comprised of charge storage devices.

So configured, an object having asperities on its surface can be placed in contact with the fingerprint contact surface. The electrical devices retain a pre-existing charge or are discharged in direct correspondence to the pattern of the asperities. As a result, the asperity pattern is both sensed and stored simultaneously. Little or no significant post sensing computational processing is required to render the sensed information suitable for storage as it can be stored in exactly the same memory cells that sensed the pattern. Very thin form factors can also be readily accommodated, and the overall device can be rendered at a price point that is at least one order of magnitude less than the least expensive presently available prior art counterpart.

Figure 1:
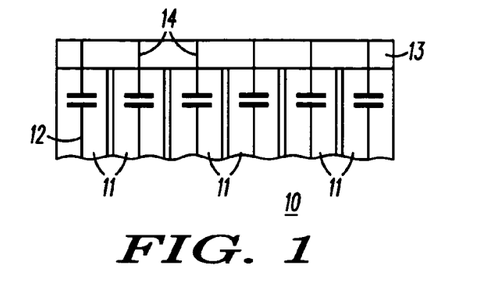
FIG. 1 illustrates a side elevational schematic view of a device configured in accordance with an embodiment of the invention.

Referring now to FIG. 1, a fingerprint capture device is generally comprised of a plurality of memory cells 11 that each include at least one charge storage device 12 in accordance with well understood prior art technique. In one embodiment, this memory comprises a solid-state memory such as, for example, a random access memory. In a more particular embodiment, the memory can be comprised of a static random access memory. In such a memory, the charged state of the charge storage device 12 represents the logical 1 or 0 that is stored within that corresponding memory cell. A fingerprint contact surface 13 is disposed over the memory cells 11. The fingerprint contact surface has a plurality of conductive paths 14 formed through it such that at least some of the conductive paths 14 are conductively coupled to at least some of the charge storage devices 12. So configured, and as related in more detail below, a conductive path exists between the exterior surface of the fingerprint contact surface 13 and the individual charge storage devices 12 that comprise the memory.

Figure 2:
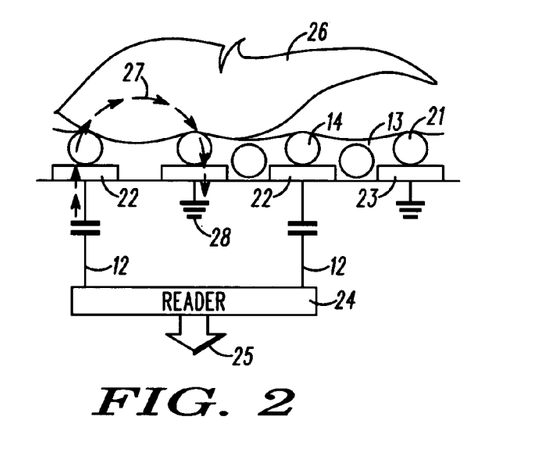
FIG. 2 illustrates a side elevational detailed schematic view of a device configured in accordance with an embodiment of the invention.

Referring now to FIG. 2 a more detailed presentation of an embodiment of a fingerprint capture device 10 will be presented. As shown in this depiction, each charge storage device 12 electrically couples to a conductive surface 22 as formed on an exterior surface of the memory. These conductive surfaces 22 comprise electrode pads and may be formed of any appropriate conductive material. Preferably, these conductive surfaces 22 are gold plated (the fingerprint contact surface will provide mechanical and chemical protection as regards these conductive surfaces 22 but some amount of moisture will still likely penetrate the fingerprint contact surface; the goldplating will aid in preventing debilitating corrosion of the conductive surfaces 22). In addition, some of the conductive surfaces 22 are coupled to a common rail 28. As depicted, the conductive surfaces 22 are shown to alternate with respect to being coupled to the charge storage devices 12 and the common rail 28. Other arrangements and ratios are possible and may in fact provide improved performance in a given application context. In this embodiment, though not drawn to scale, the conductive surfaces are square pads approximately two thousands of an inch per side.

For a fingerprint capture device 10 intended for use in sensing fingertip fingerprints, the fingerprint contact surface 13 can be approximately 0.5 mm in width by 0.5 mm in length. The memory cells with their corresponding charge storage devices 12 and conductive surfaces 22 would be disposed in an array to assure suitable sensor coverage of the entire portion of the fingerprint contact surface 13 where contact with an object is anticipated. Such an embodiment may, for instance, be used in more secure government applications. However, in another embodiment the invention may be used primarily in commercial applications, wherein the fingerprint capture device is a "swipe sensor" and the contact surface has a different aspect ratio with dimensions such as, approximately 16.5 mm×1.5 mm. Moreover, typically the dimensions of the fingerprint capture device are substantially the same as the dimensions of the smartcard's single IC chip. In addition, the fingerprint portion of the IC chip may be accessible through an opening in the backside of the smartcard.

The fingerprint contact surface 13 is comprised, in this embodiment, of an epoxy material. More particularly the fingerprint contact surface 13 is comprised of an anisotropic material. The electrically conductive paths 14 as formed through the fingerprint contact surface 13 are comprised, in this embodiment, by conductive spheres 21. In this embodiment, the conductive spheres 21 are approximately seven millionths of a meter in diameter (the spheres are not shown to scale in the drawing) and are comprised of nickel. Spheres of such material have been included in so-called conductive epoxy materials in the past. In those past embodiments, however, such spheres have been coated with a high-quality conductor such as silver or gold. Here, the nickel spheres are not coated with such a conductor. Instead, a nickel oxide coating typically forms about the sphere. As a result, although the spheres will conduct electricity the spheres also present considerable resistance to the flow of electricity. Although this approach is highly contrary to prior thinking, at least some benefits of this embodiment will be made more clear below.

Figure 3:
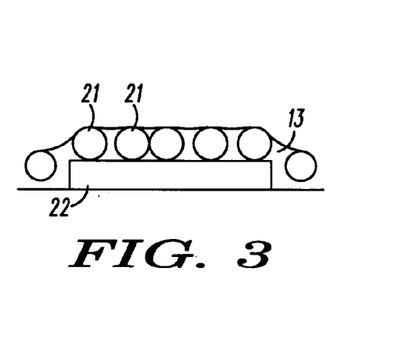
FIG. 3 illustrates a side elevational detailed view of a device configured in accordance with an embodiment of the invention.

When the epoxy material that includes the conductive spheres 21 is deposited on the memory (including the conductive surfaces 22) one or more of the conductive spheres 21 will likely be positioned proximal to one of the conductive surfaces 22. In fact, as depicted in FIG. 3, a plurality of conductive spheres 21 are likely to be positioned proximal to any given conductive surface 22. For example, presuming the conductive surface 22 and conductive sphere 21 dimensions as set forth above, and presuming a sphere doping ratio of 15 to 25 percent, there will be approximately 8 to 12 conductive spheres 21 in contact with each conductive surface 22. This level of redundancy assures that all conductive surfaces 22 (and their corresponding memory cells 11) will be active and available for the fingerprint sensing and storage process.

As related below, the epoxy comprising the fingerprint contact surface 13 is both compressed and cured. Such compression and curing, however, may not insure that an exposed portion of the spheres 21 reliably results. Therefore, and with momentary reference to FIG. 4, the exterior surface of the fingerprint contact surface 13 can be treated to expose a portion 41 of the conductive spheres 21. For example, abrasion or plasma cleansing can be utilized to achieve this result.

Figure 4:
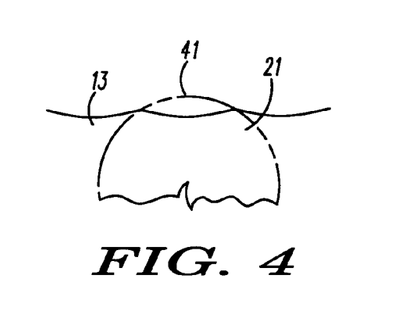
FIG. 4 illustrates a side elevational detailed view of a device configured in accordance with an embodiment of the invention.

In accordance with well understood prior art technique, the charge storage devices 12 are operably coupled to a reader 24 which it self couples to a data bus 25. So configured, the charged or discharged state of the charge storage devices 12 can be ascertained by the reader 24 and the results provided via the bus 25 to other components and elements as appropriate to a given application. In the present invention, the reader functionality and the data bus are included in the smartcard circuitry.

The above described fingerprint capture device 10 functions to simultaneously sense and store tactile impressions information regarding asperities on the surface of an object that contacts the fingerprint contact surface 13. In particular, when an object 26 contacts the fingerprint contact surface 13, protruding aspects of the surface of the object 26 will contact some of the conductive spheres 21 (in the example depicted, two adjacent conductive spheres 21 are so contacted). When this occurs, current 27 can flow from the previously charged charge storage device 12 and the conductive surface 22 as corresponds thereto, through the conductive sphere 21 that is in conductive contact with the conductive surface 22, through the object 26 itself, and through another conductive sphere 21 conductive surface 22 pair to reach the common rail 28. This, of course, will result in discharging that particular charge storage device 12.

Charge storage devices 12 that couple to conductive spheres 21 that do not contact the object 26 will not be discharged and will retain their pre-existing charge. As a result, the fingerprint capture device 10 functions to simultaneously sense asperities on the object by discharging charge storage devices 12 that correspond by location to raised features on an object and to store that sensed information as the discharged and charged states of the array of charge storage devices 12. The discharging phenomena will occur quickly which means that the sensing and storage action can occur quickly as well (sensing windows on the order of 1/100th of a second should be readily attainable). As a result, precise sensing is achievable with even untrained or otherwise inattentive users.

Figure 5:
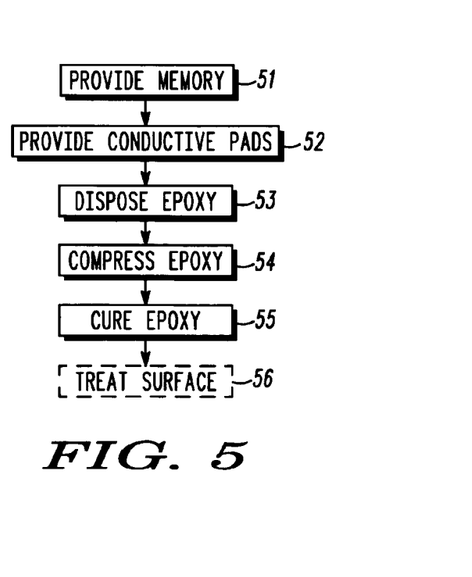
FIG. 5 illustrates a flow diagram in accordance with an embodiment of the invention.

The above device 10 can be provided in various ways. Referring to FIG. 5, a memory is provided 51 that includes a plurality of memory cells that each include at least one charge storage device. A plurality of exposed conductive pads are then provided 52 on a surface thereof. These conductive pads are provided with conductive connections, for instance wirebonds or tape automated bonding (tab) bonds, to the charge storage devices. An anisotropic epoxy containing conductive spheres is then disposed 53 over the memory and the conductive pads and compressed 54 in accordance with well understood prior art technique. This epoxy material can then be cured 55 (for example, by heating for five minutes at 150 degrees Celsius). If desired, the surface can then be treated 56 by abrasion, plasma cleansing, or other treatment that will serve to remove a portion of the epoxy material to thereby expose a conductive surface of the conductive spheres. This process can be employed at the die level if desired or at a higher level of manufacturing completion when appropriate.

Figure 6:
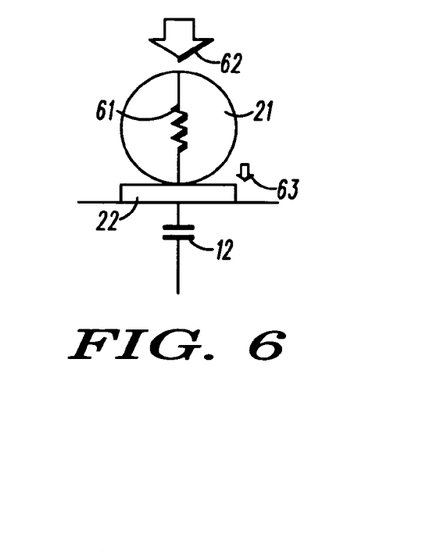
FIG. 6 illustrates a side elevational detailed schematic view of a device configured in accordance with an embodiment of the invention.

As noted earlier, certain prior art fingerprint capture methodologies are subject to electrostatic discharge and require relatively expensive protection from such discharges. The present embodiment features integral protection from electrostatic discharge. Referring to FIG. 6, the conductive spheres 21, being comprised of nickel and typically having an exterior surface comprised of nickel oxide, presents considerable electrical resistance 61. This resistance 61 is not so large as to impede the discharge of a charge storage device 12 in accordance with the methodology described above. The resistance 61 is, however, large enough to significantly attenuate an electrostatic discharge. Consequently, a large electrostatic discharge 62 will be reduced to a significantly smaller surge 63 (or dissipated completely) prior to reaching the conductive surface 22 and the charge storage device 12 that might otherwise be harmed by the electrostatic discharge 62.

The above embodiments provide for a fingerprint capture device 10 that is relatively small and inexpensive, effective, thin, relatively low power, and easily interfaced with existing processor technologies such as contained within the smart card circuitry of the present invention. As a result, this fingerprint capture device 10 can be readily and economically utilized with a variety of existing mechanisms to imbue such mechanisms with, for example, user identification verification.

Figure 7:
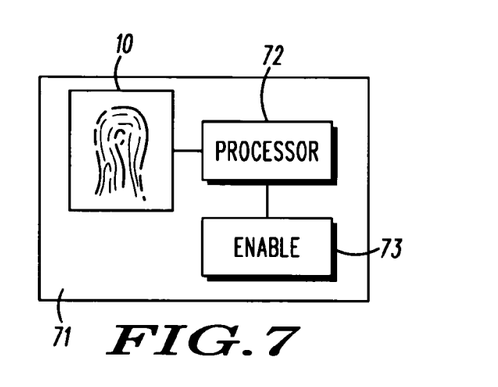
FIG. 7 illustrates a block diagram depiction of a device configured in accordance with an embodiment of the invention.

With reference to FIG. 7, a mechanism 71 having an enabled and disabled state as controlled by an enable feature 73 such as, for instance, a suitable switching device and a processor 72 to control the enable features 73 can be readily integrally combined with the fingerprint capture device 10. So configured, enablement of the device 71 can be personalized to one or more verified users. Use by a particular verified user can be assured by placement of the user's finger on the fingerprint capture device 10. Because of the various physical, performance, and economic benefits of this fingerprint capture device 10, a smartcard device 71, wherein processor 72 and enable device 73 may be included in the smartcard circuitry on the single IC chips that also includes the fingerprint authentication system, can be accommodated. The smartcard device may be, but is not limited to, credit card, debit card, or other identity or information card including passports, driver's licenses, and medical history cards.

Figure 8:
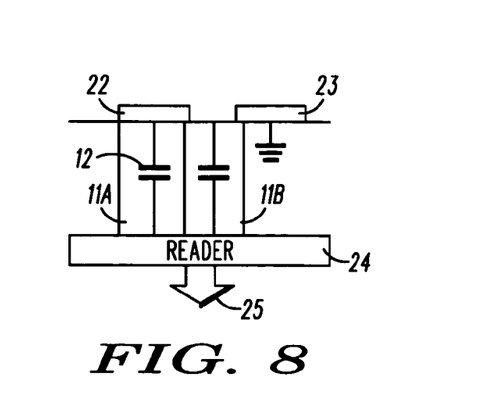
FIG. 8 illustrates a side elevational detailed schematic view of a device configured in accordance with an alternative embodiment of the invention.

Other embodiments are within the scope of these teachings. For example, with reference to FIG. 8, not every memory cell need necessarily couple to a conductive surface 22 or 23. While some memory cells 11A are coupled to a corresponding conductive surface 22 in order to sense and store fingerprint information as described above, other memory cells 11B can function as ordinary memory cells that are written to in accordance with ordinary prior art technique. In this way, some of the memory cells 11A are directly responsive to objects contacting the fingerprint contact surface 13 while other memory cells 11B are available to store other information. For example, a user's personal information (such as a social security number, etc.) and a reference set of data representing tactile impressions information against which presently sensed and stored information can be compared is storable in the latter category of memory cells 11B.

Figure 9:
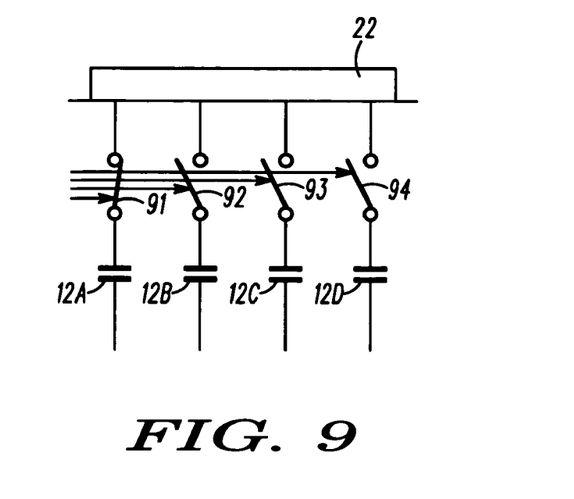
FIG. 9 illustrates a side elevational detailed schematic view of a device configured in accordance with an alternative embodiment of the invention.

Referring to FIG. 9, in another embodiment, each conductive surface 22 can potentially connect to any of a plurality of charge storage devices 12A through 12D (four such charge storage devices are depicted in FIG. 9; fewer or more such charge storage devices can be similarly accommodated). Each such charge storage device 12A through 12D has a corresponding switch 91 through 94, which switch can be controlled by an appropriate memory controller, processor, or the like. As depicted, only one switch 91 is closed such that only one charge storage device 12A is electrically coupled to the conductive surface 22. So configured, only this first charge storage device 12A will be available to discharge when operating this device to capture fingerprint information. By opening this first switch 91 and then closing the second switch 92, for example, a second sensing and capture of fingerprint information can be conducted without losing information that is stored in the first charge storage device 12A. In this way, multiple samplings of a given fingerprint can be effected without losing information and without necessarily requiring complicated or time-consuming signal processing and storage protocols.

Figure 10:
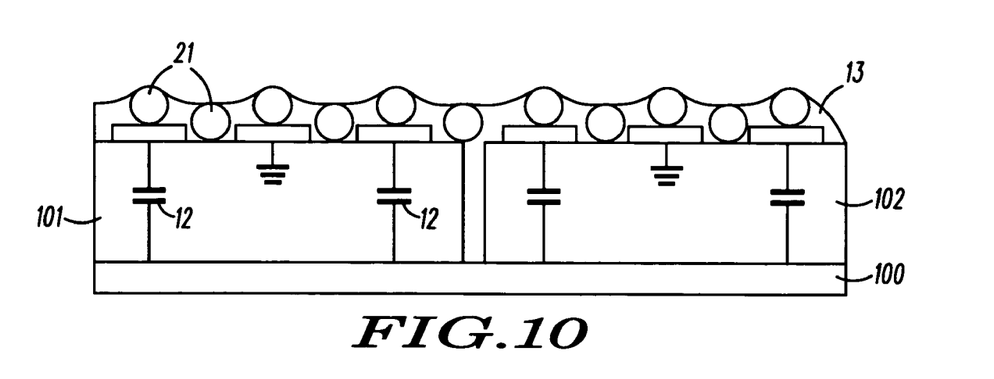
FIG. 10 illustrates a side elevational detailed schematic view of a device configured in accordance with an alternative embodiment of the invention.

Referring to FIG. 10, in another embodiment, multiple memory dies 101 and 102 can be utilized in conjunction with a single fingerprint contact surface 13 to form a single fingerprint capture device 10 (only two such dies are shown in this embodiment; more typically, a large number of individual dies would likely be utilized to support a functionally useful fingerprint contact surface area). These multiple dies 101 and 102 can be supported on a common frame or substrate 100 as appropriate to the particular application. These multiple dies 101 and 102 can share a common reader and bus or can function as independent memory elements as appropriate to the application.

One method for manufacturing a fingerprint based smartcard having a single IC, in accordance with the present invention is as follows. Take an existing Smart Card IC. Depending on the application desired, you may enlarge the IC to the size of a slap sensor, for example 0.75 inches by 0.75 inches, or change the layout to a rectangular piece and enlarge it to the size of a swipe sensor. Add an array of 2 mil×2 mil aluminum pads on the surface of the Smart Card IC. Connect a set of the pads, for example 90% of them, to gates internal to the device. Connect, for example, 10% of the pads to ground connections internal to the device. This comprises the resistive-discharge fingerprint sensor described above. Laminate a rectangle of B-stage cured anisotropic conductive coating (ACC) on top of the pad area, which provides mechanical and ESD protection as described above. Leave open the original I/O's to the IC. Cure ACC. Connect the Smart Card IC to the rest of the card using a conventional assembly process. Prepare a Smart Card housing with an opening to the ACC coated Resistive Discharge area. Package the IC and circuitry in the housing.

The fingerprint functionality is initialized by placing a finger in the opening to the ACC coated Resistive Discharge area or by swiping the finger over the sensor area to capture an initial fingerprint image of an owner of the card. The owner of the card is verified at a later time by placing a finger in the opening to the ACC coated Resistive Discharge area or swiping the finger over the sensor again. Conventional AFIS(Automatic Fingerprint Identification System) software is used for on-board (i.e., Match/On-Card), wherein the AFIS software may be stored in memory cells common to the fingerprint module and the smartcard circuitry, or the AFIS software may be used for remote matching. The ACC coated pads may also be used to turn on and off the sensor using the ACC as a switch for reducing power consumption. A subset of pads can be continually monitored. When the state of those pads changes, the other pads can be initialized and read thereby turning on the device. Other methods for manufacturing a fingerprint based smartcard in accordance with the present invention may be envisioned by those of ordinary skill in the art.

Figure 11:
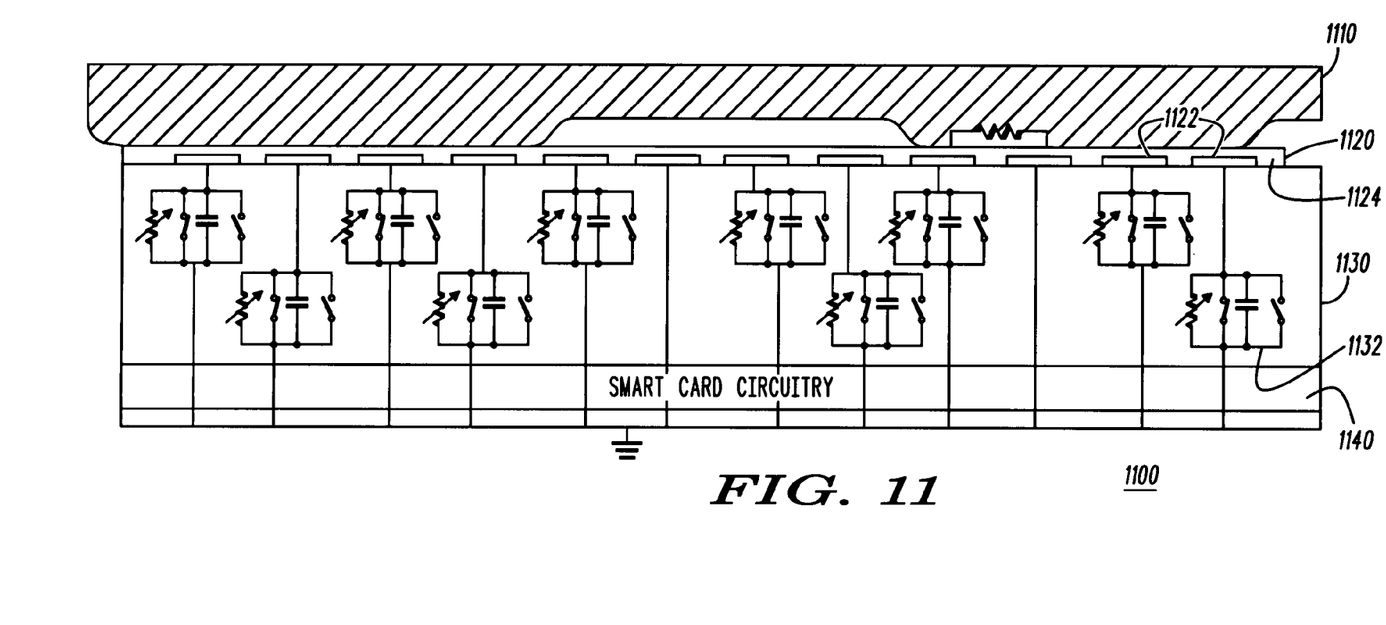
FIG. 11 illustrates a side elevational detailed schematic view of a fingerprint based smartcard in accordance with the present invention.

FIG. 11 illustrates a side elevational detailed schematic view of a fingerprint based smartcard IC 1100 in accordance with an embodiment of the present invention. Shown is a portion of a finger 1110 touching the fingerprint sensor 1120 that includes the ACC coated Resistive Discharge area 1124 and a plurality of contacts 1122. The IC also comprises memory 1130 having a plurality of memory cells 1132. Finally, IC 1100 comprises conventional smartcard circuitry known in the art.

Figure 12:
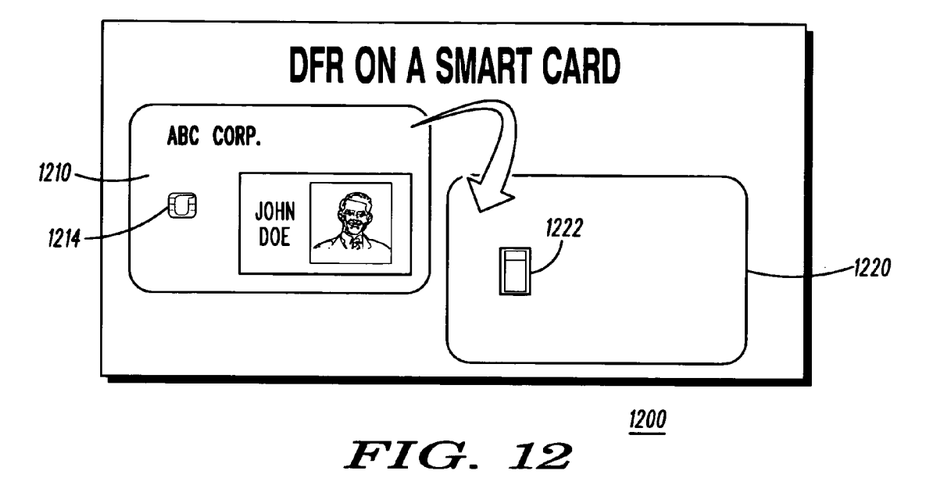
FIG. 12 illustrates a fingerprint based smartcard in accordance with an embodiment of the present invention.

FIG. 12 illustrates a fingerprint based smartcard 1200 in accordance with an embodiment of the present invention. Shown is the frontside 1210 of the smart card with a portion of the single IC 1222 connected to at least one gold contact pads 1214 for the smartcard functionality. Further shown is the backside 1220 of the smart card with a portion of the single IC 1222 exposed for the sensor functionality.

Figure 13:
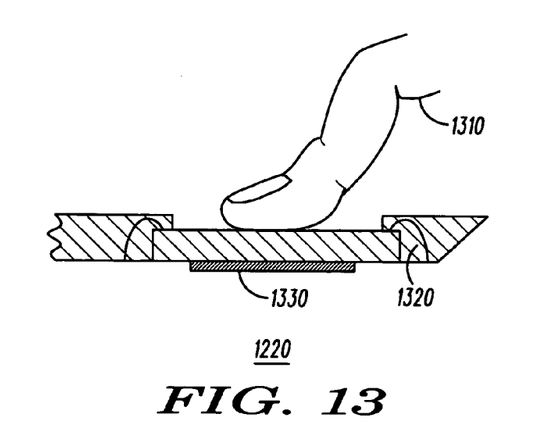
FIG. 13 illustrates an exploded view of the backside of the smartcard of FIG. 12.

FIG. 13 illustrates an exploded view of the backside 1220 of the smartcard of FIG. 12, wherein a portion of a finger 1310 is touching the fingerprint sensor 1320 on the smartcard IC, which is connected to the gold contact pads 1330.

Improved asperity detection functionality may be added to the single IC chip in another embodiment of the present invention. Generally speaking, pursuant to these various embodiments, asperity detection occurs over time. This permits characterizing a given asperity with respect to its topographic characteristics (and also, if desired, the topographic characteristics of the surface that supports the asperity). Such information can be used to characterize the asperity with respect to its apparent three-dimensional form factor. Such information can also be used to characterize the elasticity of the asperity (as the asperity is brought into contact with an asperity detection surface) and/or the resiliency of the asperity (as the asperity is removed from contact with an asperity detection surface).

Pursuant to one embodiment, points of contact between one or more asperities and an asperity detection surface are noted at a first time. At a later time (preferably a small fraction of a second later) the points of contact are again noted, with additional readings being taken and captured as desired and/or appropriate to a given application. The resultant information can then be used as suggested above to provide the temporally based asperity characterizing data.

This approach does not necessarily require increased asperity detection imaging resolution and therefore avoids at least most of the concerns that hamper adoption of other techniques that are intended to improve accuracy. Notwithstanding this benefit, these embodiments nevertheless contribute additional meaningful characterizing content that can significantly improve the accuracy and reliability of asperity-based identification and verification. In effect, then, improved accuracy based upon additional feature information is attained without a commensurate increase in resolution complexity.

Figure 14:
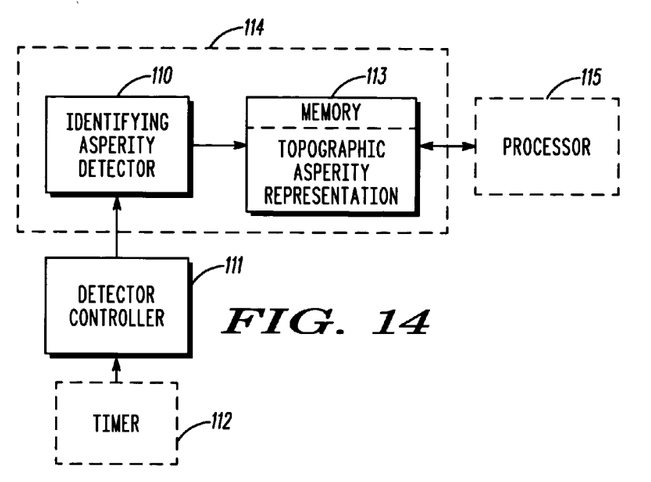
FIG. 14 illustrates a block diagram of an asperity detection device as configured in accordance with an embodiment of the invention.

Referring now to the drawings, FIG. 14 presents a block diagram view of a platform to support the desired topographically and/or temporally-based asperity detection. A variety of identifying asperity detectors 110 can possibly serve for these purposes, but for a preferred embodiment, the identifying asperity detector 110 comprises a resistive discharge direct asperity reader as described above.

Such an asperity detector is generally comprised of a plurality of memory cells that each include at least one charge storage device. In the present invention, the memory is shared with the fingerprint capture device and the smartcard circuitry and is described above. When an object contacts the fingerprint contact surface, protruding aspects of the surface of the object will contact some of the conductive spheres and current will flow from the previously charged charge storage device and the conductive surface as corresponds thereto, through the conductive sphere that is in conductive contact with the conductive surface, through the object itself, and through another conductive sphere-conductive surface pair to reach the common rail. This, of course, will result in discharging that particular charge storage device. The discharged state of the charge storage device then serves as a characterizing indicator of the existence of the asperity at a particular location of the fingerprint contact surface.

Referring again to FIG. 14, the above described identifying asperity detector 110 serves to simultaneously sense and store tactile impressions information regarding asperities on the surface of an object that contacts the asperity contact surface. A detector controller 111 couples to the identifying asperity detector 110 and serves to control, for example, when and how the detector 110 operates (for example, by controlling charging of the charge storage devices of the detector 110). In these embodiments, the identifying asperity detector 110 captures a rapid series of asperity detection images. To facilitate this, the detector controller 111 can either include an integral timer or an outboard timer 112 can optionally be used instead. Such a timer (either internal or outboard) permits determination of predetermined time intervals, such as intervals as small as one one-hundredth or one-thousandth of a second in duration, to be accurately and reliably determined for use by the detector controller 111 as described below.

These embodiments preferably provide a memory to retain the results of the series of temporally spaced asperity detection events. This memory can fully or partially comprise an outboard memory 113 but is typically fully integrated with the identifying asperity detector 110 and is implemented as the shared memory on the single IC chip. In a preferred embodiment, when the identifying asperity detector 110 comprises a resistive discharge reader, the memory can at least largely comprise the charge storage devices of the reader itself.

If desired, a processor 115 can be included to permit subsequent processing of the asperity information. For example, topographic asperity representation information as retained in the memory 113 can be accessed by such a processor 115 to effect desired identification and/or authorization activities. In the present invention, processor 115 would typically be the shared processor included in the smartcard circuitry on the single IC chip.

So configured, such a platform generally serves to provide at least one identifying asperity detector, a detector controller having a control output that operably couples to the identifying asperity detector to permit control thereof, and a memory operably coupled to the identifying asperity detector to permit, for example, the storage of topographic representations of the asperities of a given surface such as a fingertip. The topographic representations, as shown below in more detail, derive at least in part from temporally-spaced asperity detection events that together provide a composite topographic representation. As also will be shown below, such a platform can further capture such temporally-spaced asperity detection events to permit characterization as a function of elasticity and/or resiliency of the asperities and the underlying surface of the asperities.

Figure 15:
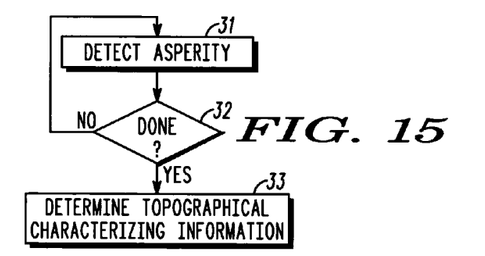
FIG. 15 illustrates a flow diagram as configured in accordance with an embodiment of the invention.

Referring now to FIG. 15, the platform described (or such other enabling platform as may be desired) repeatedly detects asperities (steps 31 and 32) on an external surface (such as a fingertip) over a short period of time. Such asperities can be, for example, the friction ridges that define fingerprints, palm prints, leather glove patterns, and the like. More particularly, in a preferred embodiment, such asperities are detected, at different times (by detecting a proximity relationship between such identifying asperities and a detection surface such as the ones described earlier), such detections are used to determine topographical characterizing information (step 33).

Figure 16:
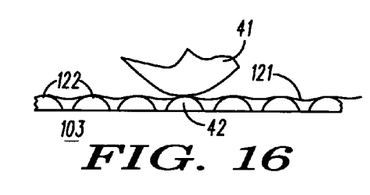
FIG. 16 illustrates a side-elevational detailed schematic view of an asperity initially contacting an asperity detector as configured in accordance with an embodiment of the invention.
Figure 17:
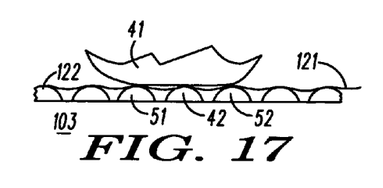
FIG. 17 illustrates a side-elevational detailed schematic view of the asperity contacting an asperity detector at a later time as configured in accordance with an embodiment of the invention.

To illustrate, and referring now to FIG. 16, at a first moment in time when an external surface (such as a fingertip) approaches the asperity detector 103, an outermost portion of a given asperity 41 on the external surface makes first contact with a responsive portion 122 of the asperity contact surface 121 (in particular, in this embodiment, a specific conductive sphere 42). Such points of contact serve to detect and provide an indication of a corresponding asperity feature. As the external surface continues to move towards the asperity detector 103, the asperity 41 compresses (as suggested in FIG. 17). Such compression frequently causes the asperity 41 to contact other adjacent or nearby conductive spheres (51 and 52 in this example) at a slightly later point in time from the moment captured in FIG. 16. By capturing this later information, the process captures additional asperity information.

Figure 18:
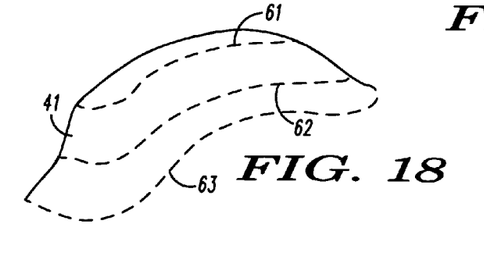
FIG. 18 illustrates a perspective view of an illustrative asperity.
Figure 19:
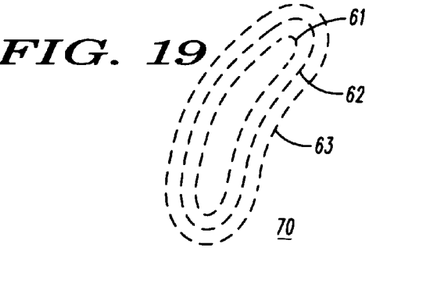
FIG. 19 illustrates a top plan view of illustrative topographic characterizing information for the asperity of FIG. 18 as configured in accordance with an embodiment of the invention.

With reference to FIGS. 18 and 19, it can be seen that different portions of a given asperity 41 are detected at different times as the material comprising the asperity becomes compressed against the asperity detector 103. In particular, the most outwardly extending portions of the asperity tend to first contact the detector 103 with other portions contacting the detector 103 at later times. For example, in the simple example illustrated, a most outward portion 61 of the asperity 41 will contact the detector 10 first, followed at a later time by a less outward portion 62 of the asperity 41, which is followed yet later by an even less outward portion 63 of the asperity 41. By noting which portions of the detector surface are contacted by the asperity at each given time, the resultant data can be used to determine a topographical representation 70 of the asperity as illustrated in FIG. 19. Such a representation provides information not only with respect to a general two dimensional configuration of the asperity (as is otherwise typically provided by most other asperity detection schemes) but also the three dimensional configuration thereof.

Such three dimensional topographic representations provide meaningful characterizing information regarding the identifying asperities of, for example, an individual. Such information can therefore be used to increase the reliability and accuracy of an asperity-based identification process.

Figure 20:
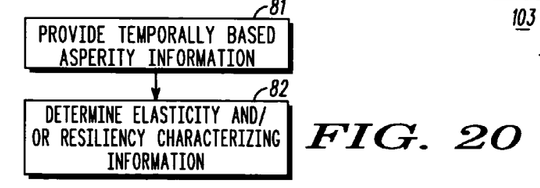
FIG. 20 illustrates a flow diagram as configured in accordance with an embodiment of the invention.

Such information can also be used to characterize asperities (and/or the underlying external surface that supports the asperities) in other ways. For example, with reference to FIG. 20, following provision 81 of such temporally-based asperity information, elasticity and/or resiliency characterizing information for the asperity can also be determined 82. By detecting at various times a predetermined level of proximity (such as actual physical contact) between the asperity detection sensors and the asperity itself while the asperity is brought into proximity with the detector, elasticity characteristics of the asperity and/or the underlying surface of the asperity can be ascertained. In a similar manner, resiliency characteristics of the asperity and/or the underlying surface of the asperity can be ascertained by noting the same kinds of proximity relationships at various times as the asperity is removed from proximity with the detector. In particular, such characteristics reveal themselves as, over time, portions of the asperity make contact (or break contact) with the detector surface as a function of elasticity and/or resiliency of the asperity itself and/or the underlying support surface.

Thus, using this asperity detection/characterizing mechanism, as the fingerprint of an individual is moved with respect to such a fingerprint reader surface, the detector 110 can capture a series of representations of the friction ridges that have at least a predetermined degree of proximity, such as full physical contact, with the fingerprint reader surface at a time when the corresponding representation is captured. The resultant series of representations can then be used to form a topographic characterization of the fingerprint. Such a series of representations can be captured as the fingerprint moves towards the fingerprint reader surface, away from the fingerprint reader surface, or during both events.

The resolution of the resultant temporally-based information comprises a function, at least in part, of the duration of the time intervals between capturing such information. Resistive discharge direct asperity readers are potentially capable of reacting to capture intervals as brief as one thousandth of a second. For many purposes, however, useful and improved results can be obtained with considerably longer intervals between capture events.

The various embodiments set forth herein for asperity detection apparatus and methods all tend to provide increased quantities of characterizing information without requiring an increase with respect to two dimensional imaging resolution. As a result, accuracy and reliability can be increased without occasioning a commensurate increase with respect to, for example, the imaging resolution of a given approach. The three dimensional and/or time-based characterization of an asperity also serves to more completely characterize a given asperity and hence renders fraudulent activity less likely to succeed.

The resistance-based sensor is an enabling technology for the integration of sensor functionality with smart card functionality because the technology utilizes only the existing RAM cells that comprise the memory in a smart card. No additional processes are required other than bringing vias to the surface for contact I/O's in the manner that wirebond I/O's are already brought to the surface of the die. For this reason there is a low cost for implementation.

Integration of the resistive-based sensor with the smart card circuitry provides the added security that is desired by eliminating external connections between the two functional devices.

Another advantage of combining the smartcard IC and the resistive-based sensor is power reduction. Since the RAM transistor functions both for memory and for pixel capture, a single quiescent current is used. Secondly there is no power requirement to run the interconnect circuitry between the sensor and the smartcard chip. Together these reduce the overall system power consumption and budget.

In a situation where RF connectivity is required for smart card interconnect rather than a contactless card, an integrated sensor and smartcard chip is necessary in order to have enough area to provide a lower frequency antenna or a longer antenna for higher gain.

While the invention has been described in conjunction with specific embodiments thereof, additional advantages and modifications will readily occur to those skilled in the art. The invention, in its broader aspects, is therefore not limited to the specific details, representative apparatus, and illustrative examples shown and described. Various alterations, modifications and variations will be apparent to those skilled in the art in light of the foregoing description. Thus, it should be understood that the invention is not limited by the foregoing description, but embraces all such alterations, modifications and variations in accordance with the spirit and scope of the appended claims.

What is claimed is:

1. A fingerprint based smartcard comprising:
   a fingerprint module comprising a fingerprint capture device, a first processor and a first memory operatively coupled for capturing an initial fingerprint of a user and at least one subsequent fingerprint of the user and for comparing the at least one subsequent fingerprint to the initial fingerprint; and
   smartcard circuitry comprising a second processor, a second memory and a communication element operatively coupled together and to the fingerprint module for receiving results of the comparison and communicating the result to a host system wherein the fingerprint module and the smartcard circuitry are co-located on a common integrated circuit chip, wherein the fingerprint capture device comprises: the first memory comprising a first plurality of memory cells wherein each memory cell has a corresponding electrical device; and a fingerprint contact surface disposed substantially coplanar to the first memory wherein the fingerprint contact surface has a plurality of conductive paths formed through the fingerprint contact surface and wherein at least some of the conductive paths are substantially directly conductively coupled to at least some of the corresponding electrical devices.

2. A fingerprint based smartcard in accordance with claim 1, wherein the second memory comprises a second plurality of memory cells wherein each memory cell has a corresponding electrical device, wherein the first plurality of memory cells comprises at least a portion of the second plurality of memory cells.

3. A fingerprint based smartcard in accordance with claim 1, wherein the first and the second processors are the same processor.

4. A fingerprint based smartcard in accordance with claim 1, wherein the fingerprint capture device is one of a swipe sensor and a slap sensor.

5. A fingerprint based smartcard in accordance with claim 1, wherein the fingerprint capture device has first dimensions and the common integrated circuit chip has second dimensions that are substantially equal to the first dimensions.

6. A fingerprint based smartcard in accordance with claim 1 further comprising a housing having a frontside and a backside for enclosing the fingerprint module and the smartcard circuitry, wherein the backside of the housing includes an opening for exposing at least a portion of the fingerprint capture device.

7. A fingerprint based smartcard in accordance with claim 6 further comprising at least one contact pad coupled to the frontside of the housing, wherein the smartcard circuitry is operatively coupled to the at least one contact pad for enabling the smartcard circuitry to communicate with the host system.

8. A fingerprint based smartcard in accordance with claim 1, wherein the smartcard circuitry comprises a reader for receiving the results of the comparison and a data bus for transferring the results from the reader to the communication element.

9. A fingerprint based smartcard in accordance with claim 1 further comprising an enable device coupled to the first processor for enabling at least two different users of the smartcard.

10. A fingerprint based smartcard in accordance with claim 1 that is selected from a group consisting of a credit card, a debit card and an identity card.

11. A fingerprint based smartcard in accordance with claim 10, wherein the identity card is selected from a group consisting of a passport, a driver's license and a medical history card.

12. A fingerprint based smartcard in accordance with claim 1, wherein the first memory stores Automatic Fingerprint Identification System (AFIS) software that is loaded into the first processor for comparing the at least one subsequent fingerprint to the initial fingerprint of the user.

13. A fingerprint based smartcard in accordance with claim 1, wherein the communication element enables contact-less communication between the smartcard circuitry and the host system.

14. A fingerprint based smartcard in accordance with claim 1 further comprising an asperity detector coupled to the first memory and the first processor.

15. A fingerprint based smartcard in accordance with claim 14 further comprising a detector controller coupled to the asperity detector and a timer coupled to the detector controller for controlling the asperity detector.

16. A fingerprint based smartcard comprising:
a fingerprint module comprising:
a fingerprint capture device, comprising:
a first memory for capturing an initial fingerprint of a user and at least one subsequent fingerprint of the user the first memory comprising a first plurality of memory cells wherein each memory cell has a corresponding electrical device; and
a fingerprint contact surface disposed substantially coplanar to the first memory wherein the fingerprint contact surface has a plurality of conductive paths formed through the fingerprint contact surface and wherein at least some of the conductive paths are substantially directly conductively coupled to at least some of the corresponding electrical devices; and
a first processor operatively coupled to the fingerprint capture device for comparing the at least one subsequent fingerprint to the initial fingerprint; and
smartcard circuitry comprising a second processor, a second memory and a communication element operatively coupled together and to the fingerprint module for receiving the results of the comparison and communicating the results to a host system, the second memory comprising a second plurality of memory cells wherein each memory cell has a corresponding electrical device, wherein the first plurality of memory cells comprises at least a portion of the second plurality of memory cells.

17. A fingerprint based smartcard in accordance with claim 16, wherein the fingerprint module and the smartcard circuitry are co-located on a common integrated circuit chip.

18. A fingerprint based smartcard in accordance with claim 16, wherein the first and the second processors are the same processor.

19. A fingerprint based smartcard in accordance with claim 16 further comprising:
a housing having a frontside and a backside for enclosing the fingerprint module and the smartcard circuitry, wherein the backside of the housing includes an opening for exposing at least a portion of the fingerprint capture device; and
at least one contact pad coupled to the frontside of the housing, wherein the smartcard circuitry is operatively coupled to the at least one contact pad for enabling the smartcard circuitry to communicate with the host system.

* * * * *